(12) United States Patent
Hermannsson et al.

(10) Patent No.: US 10,141,675 B2
(45) Date of Patent: *Nov. 27, 2018

(54) BIOMETRIC BELT CONNECTOR

(71) Applicant: NOX MEDICAL, Reykjavik (IS)

(72) Inventors: Kormakur Hlini Hermannsson, Reykjavik (IS); Sveinbjorn Hoskuldsson, Reykjavik (IS)

(73) Assignee: NOX MEDICAL, Reykjavik (IS)

( * ) Notice: Subject to any disclaimer, the term of this patent is extended or adjusted under 35 U.S.C. 154(b) by 0 days.

This patent is subject to a terminal disclaimer.

(21) Appl. No.: 15/394,246

(22) Filed: Dec. 29, 2016

(65) Prior Publication Data

US 2017/0110823 A1    Apr. 20, 2017

Related U.S. Application Data

(63) Continuation of application No. 14/733,774, filed on Jun. 8, 2015, now Pat. No. 9,537,246, which is a
(Continued)

(51) Int. Cl.
*H01R 11/22* (2006.01)
*A61B 5/00* (2006.01)
(Continued)

(52) U.S. Cl.
CPC .............. *H01R 13/46* (2013.01); *A61B 5/00* (2013.01); *A61B 5/0004* (2013.01);
(Continued)

(58) Field of Classification Search
CPC .... H01R 13/46; H01R 13/6683; H01R 11/22; H01R 13/717; H01R 43/00; H01R 43/18;
(Continued)

(56) References Cited

U.S. PATENT DOCUMENTS 937,130 A    10/1909  Williams
1,001,054 A    8/1911  Lawrence
(Continued)

FOREIGN PATENT DOCUMENTS

DE    199 41 500 A1    3/2001
DE    19941500 A1    3/2001
(Continued)

OTHER PUBLICATIONS

Attachment A, To Natus' Third Supplemental Invalidity and Unenforceability Contentions, U.S. Pat. No. 9,059,532, *Nox Medical Ehf.* v. *Natus Neurology, Inc.*, Civil Action No. 15-cv-00709-RGA (D. Del), 63 Pages.
(Continued)

*Primary Examiner* — Harshad C Patel
(74) *Attorney, Agent, or Firm* — Workman Nydegger

(57) ABSTRACT

A belt connector is provided. The belt connector is configured to electrically connect a conductor of an electrode belt to a male portion of a snap connector electrode connected to a biometric device. The belt connector includes a frame, a fastener, and an engaging member. The frame includes a receiving hole having radial flexibility. The receiving hole is configured to receive and fasten the frame to a protrusion of the male portion of the snap connector electrode. The fastener is configured to fasten the frame to a first end of the electrode belt. The engaging member is adjacent to the receiving hole and engages the conductor of the electrode belt by the conductor passing through the receiving hole. When the male portion of the snap connector electrode penetrates the receiving hole, the conductor is forced into contact with a lateral surface of the male portion of the snap connector electrode.

20 Claims, 4 Drawing Sheets

Related U.S. Application Data continuation of application No. 13/806,834, filed as application No. PCT/IS2011/050010 on Jun. 24, 2011, now Pat. No. 9,059,532.

(60) Provisional application No. 61/358,472, filed on Jun. 25, 2010.

(51) Int. Cl.

| | | |
|---|---|---|
| *H01R 13/46* | (2006.01) | |
| *A61B 5/0428* | (2006.01) | |
| *A61B 5/08* | (2006.01) | |
| *A61B 5/113* | (2006.01) | |
| *H01R 43/00* | (2006.01) | |
| *H01R 13/6591* | (2011.01) | |
| *H01R 43/18* | (2006.01) | |

(52) U.S. Cl.
CPC ........ *A61B 5/04286* (2013.01); *A61B 5/0806* (2013.01); *A61B 5/1135* (2013.01); *A61B 5/6804* (2013.01); *H01R 11/22* (2013.01); *H01R 13/6591* (2013.01); *H01R 43/00* (2013.01); *H01R 43/18* (2013.01); *A61B 2562/227* (2013.01); *Y10T 29/49208* (2015.01)

(58) Field of Classification Search
CPC .. H01R 13/5224; H01R 2201/12; A61B 5/00; A61B 5/04286; A61B 5/0806; A61B 5/1135; A61B 5/6804
USPC ............... 439/527, 860, 859, 869, 909, 268; 368/282; 600/384
See application file for complete search history.

(56) References Cited

U.S. PATENT DOCUMENTS

| | | | |
|---|---|---|---|
| 1,115,459 | A | 10/1914 | Abizaid |
| 1,193,050 | A | 8/1916 | Orewiler |
| 2,305,277 | A | 12/1942 | Sloane et al. |
| 2,649,573 | A | 8/1953 | Goldberg et al. |
| 2,667,159 | A | 1/1954 | Goldberg et al. |
| 3,092,759 | A | 6/1963 | Sommer |
| 3,347,223 | A | 10/1967 | Pacela |
| 3,500,823 | A | 3/1970 | Richardson et al. |
| 3,560,845 | A | 2/1971 | Goldber et al. |
| 3,685,105 | A | 8/1972 | Carlile et al. |
| 4,308,872 | A | 1/1982 | Watson et al. |
| 4,373,534 | A | 2/1983 | Watson |
| 4,430,777 | A | 2/1984 | Takeda |
| 4,671,591 | A | 6/1987 | Archer |
| 4,777,962 | A | 10/1988 | Watson et al. |
| 4,807,640 | A | 2/1989 | Watson et al. |
| 4,815,473 | A | 3/1989 | Watson et al. |
| 4,817,625 | A | 4/1989 | Miles |
| 4,832,608 | A | 5/1989 | Kroll |
| 4,834,109 | A | 5/1989 | Watson |
| 1,842,557 | A | 6/1989 | Muz |
| 5,301,678 | A | 4/1994 | Watson et al. |
| 5,326,272 | A | 7/1994 | Harhen et al. |
| 5,331,968 | A | 7/1994 | Williams et al. |
| 5,348,008 | A | 9/1994 | Bornn et al. |
| 5,353,793 | A | 10/1994 | Bornn |
| 5,543,012 | A | 8/1996 | Watson et al. |
| 6,148,486 | A | 11/2000 | Uehara et al. |
| 6,327,486 | B1 | 12/2001 | Nissila et al. |
| 6,341,504 | B1 | 1/2002 | Istook |
| 6,413,225 | B1 | 6/2002 | Sackner et al. |
| 6,461,307 | B1 | 10/2002 | Kristbjarnarson et al. |
| 6,807,438 | B1 | 10/2004 | Brun Del Re et al. |
| 7,171,265 | B2 | 1/2007 | Hoium et al. |
| 7,267,652 | B2 | 9/2007 | Coyle et al. |
| 7,593,767 | B1 | 9/2009 | Modarres |
| 7,604,603 | B2 | 10/2009 | Sackner et al. |
| 7,670,295 | B2 | 3/2010 | Sackner et al. |
| 7,727,161 | B2 | 6/2010 | Coyle et al. |
| 7,762,953 | B2 | 7/2010 | Derchak et al. |
| 7,819,710 | B2 | 10/2010 | McIntire et al. |
| 7,878,979 | B2 | 2/2011 | Derchak |
| 7,914,350 | B1 | 3/2011 | Bozich et al. |
| 8,025,539 | B2 | 9/2011 | Hermannsson |
| 8,033,996 | B2 | 10/2011 | Behar |
| 8,034,001 | B2 | 10/2011 | Gal |
| 8,052,612 | B2 | 11/2011 | Tang et al. |
| 8,137,270 | B2 | 3/2012 | Keenan et al. |
| 8,165,654 | B2 | 4/2012 | Tang et al. |
| 8,177,724 | B2 | 5/2012 | Derchak et al. |
| 8,193,821 | B2 | 6/2012 | Mueller et al. |
| 8,251,736 | B2 | 8/2012 | McIntire et al. |
| 8,475,387 | B2 | 7/2013 | Derchak et al. |
| 8,579,794 | B2 | 11/2013 | Henke |
| 8,628,480 | B2 | 1/2014 | Derchak |
| 8,762,733 | B2 | 6/2014 | Derchak et al. |
| 8,777,868 | B2 | 7/2014 | Gal |
| 8,790,255 | B2 | 7/2014 | Behar |
| 8,790,272 | B2 | 7/2014 | Sackner et al. |
| 9,059,532 | B2 | 6/2015 | Hermannsson |
| 2002/0032386 | A1 | 3/2002 | Sackner et al. |
| 2002/0032388 | A1 | 3/2002 | Kristbjarnarson et al. |
| 2002/0120207 | A1 | 8/2002 | Hoffman |
| 2003/0135127 | A1 | 7/2003 | Sackner et al. |
| 2005/0054941 | A1 | 3/2005 | Ting et al. |
| 2005/0119586 | A1 | 6/2005 | Coyle et al. |
| 2006/0122528 | A1 | 6/2006 | Gal |
| 2006/0258948 | A1 | 11/2006 | Linville |
| 2006/0282001 | A1 | 12/2006 | Noel et al. |
| 2007/0167089 | A1 | 7/2007 | Gobron et al. |
| 2009/0259135 | A1 | 10/2009 | Stasz |
| 2010/0060300 | A1 | 3/2010 | Muller et al. |
| 2010/0075527 | A1 | 3/2010 | McIntire et al. |
| 2010/0075549 | A1 | 3/2010 | McIntire et al. |
| 2010/0297868 | A1 | 11/2010 | Hermannsson |
| 2011/0151728 | A1 | 6/2011 | Astola |
| 2011/0248729 | A2 | 10/2011 | Mueller et al. |
| 2012/0101357 | A1 | 4/2012 | Hoskuldsson et al. |
| 2015/0126879 | A1 | 5/2015 | Hoskuldsson et al. |
| 2015/0280348 | A1 | 10/2015 | Hermannsson |

FOREIGN PATENT DOCUMENTS

| | | |
|---|---|---|
| EP | 2324760 A2 | 5/2011 |
| EP | 2324761 A2 | 5/2011 |
| EP | 2417905 A1 | 2/2012 |
| EP | 2484276 A2 | 8/2012 |
| EP | 2484277 A2 | 8/2012 |
| EP | 2484278 A3 | 8/2012 |
| EP | 2508123 A1 | 10/2012 |
| EP | 2508124 A2 | 10/2012 |
| EP | 2584962 A2 | 5/2013 |
| EP | 2589335 A2 | 5/2013 |
| WO | 02/02013 A1 | 2/2002 |
| WO | 02/080761 A2 | 10/2002 |
| WO | 2006024024 A2 | 3/2006 |
| WO | 2006/066566 A2 | 6/2006 |
| WO | 2008102140 A1 | 8/2008 |
| WO | D071077-002 | 10/2008 |
| WO | 20080133394 A1 | 11/2008 |
| WO | 2011029136 A1 | 3/2011 |

OTHER PUBLICATIONS

International Search Report from PCT Application No. PCT/IS2011/050010, dated Feb. 29, 2012.
International Search Report from PCT Application No. PCT/IB2014/002760, dated Mar. 27, 2015.
International Preliminary Report on Patentability from PCT Application No. PCT/IB2014/002760, dated May 10, 2016.
"Opinion Regarding European Patent, 2584962", Kilbun & Strode, Mar. 11, 2015, 14 Pages.
Notice of Appeal, Western High Court, *Cephalon A/S*, VS, *Nox Medical Ehf*, Mar. 9, 2015, 10 Pages.

(56) References Cited

OTHER PUBLICATIONS

"Defendant's Preliminary Invalidity and Unenforceability Contentions," Nox Medical EHF v. Natus Neurology Inc., Defendants, Civil Action No. 1:15-cv-00709-RGA, In the United States District Court for the District of Delaware, Apr. 15, 2016, 117 Pages.
"Defendant's First Supplemental Invalidity and Unenforceability Contentions," Nox Medical EHF v. Natus Neurology Inc., Defendants, Civil Action No. 1:15-cv-00709-RGA, In the United States District Court for the District of Delaware, Dec. 1, 2016, 3 Pages.
"Defendant's Second Supplemental Invalidity and Unenforceability Contentions," Nox Medical EHF v. Natus Neurology Inc., Defendants, Civil Action No. 1:15-cv-00709-RGA, In the United States District Court for the District of Delaware, 2009, 59 Pages.
"Defendant's Third Supplemental Invalidity and Unenforceability Contentions," Nox Medical EHF v. Natus Neurology Inc., Civil Action No. 1:15-cv-00709-RGA, In the United States District Court for the District of Delaware, Feb. 17, 2017, 4 Pages.
Patent Owner's Preliminary Response to U.S. Pat. No. 9,059,532, Dec. 27, 2016. 86 Pages.
Response to Opposition for European Patent No. 2584962, Nov. 23, 2015, 154 Pages.
Cohen, Kevin P. et al., "Comparison of Impedance and Inductance Ventilation Sensors on Adults During Breathing, Motion, and Simulated Airway Obstruction", IEEE Transactions on Biomedical Engineering, vol. 44, No. 7, Jul. 1, 1997, pp. 555-565.
Cohen, K.P. et al., "Breath Detection Using a Fuzzy Neural Network and Sensor Fusion", 1995 International Conference on Acoustics, Speech, and Signal Processing, May 9-12, 1995, vol. 5, pp. 3491-3494.
Stromberg, N.O.T., "Error analysis of a natural breathing calibration method for respiratory inductive plethysmography", Medical & Biological Engineering & Computing 2001, vol. 39, No. 3, May 1, 2001, pp. 310-314.
International Search Report from International PCT Application No. PCT/IS2010/000007, dated Oct. 1, 2010.
International Search Report from International PCT Application No. PCT/IB2014/002760, dated Mar. 27, 2015.
"Disposable and Accessories Catalog for Respiratory Diagnostics", CareFusion, Natus Medical Inc., 2009, 138 Pages.
Petition for Inter Partes Review of U.S. Pat. No. 9,059,532, Sep. 15, 2016.
Dehkordi et al., "Monitoring Torso Acceleration for Estimating the Respiratory Flow and Efforts for Sleep Apnea Detection," 34th Annual International Conference of the IEEE EMBS, Aug. 28, 2012, pp. 6345-6348.
International Search Report and Written Opinion from PCT Application No. PCT/IB2017/055022, dated Nov. 17, 2017.
"Defendant's Fourth Supplemental Invalidity and Unenforceability Contentions," Nox Medical ehf v. Natus Neurology Inc., Civil Action No. 1:15-cv-00709-RGA, Mar. 22, 2017, 214 Pages.
"Natus Neurology Inc.'s Combined (1) Reply Brief in Support of Its Motion for Summary Judgment of Invalidity, (2) Brief in Opposition to Nox's Cross-Motion for Summary Judgment of No Invalidity, and (3) Brief in Opposition to Nox's Proposed Claim Constructions," Nox Medical ehf v. Natus Neurology Inc., Civil Action No. 1:15-cv-00709-RGA, Aug. 15, 2017, 416 Pages.
Statement Setting out the Grounds of Appeal from EP Application No. 11758266.8, Mar. 22, 2018, 62 Pages.
Final Written Decision, Inter Partes Review, Natus Medical Inc., Natus Neurology Inc., Embla Systems LLC, and Embla Systems Ltd., Petitioner, v. Nox Medical ehf for U.S Pat. No. 9,059,532, Mar. 21, 2018, 39 Pages.
Patent Owner's Response Under 37 C.F.R 42.120, for U.S. Pat. No. 9,059,532, Jun. 29, 2017, 238 Pages.
Petitioners' Reply Pursuant to 37 C.F.R 42.23 (Redacted—Public Version), for U.S. Pat. No. 9,059,532, Oct. 9, 2017, 38 Pages.
Memorandum Opinion from Civil Action No. 15-709-RGA, Nox Medical ehf v. Natus Neurology Inc., Feb. 13, 2018, 24 Pages.
Judgment from Civil Action No. 15-709-RGA, Nox Medical ehf v. Natus Neurology Inc., May 8, 2018, 1 Page.
Plaintiff Nox Medical's Combined (1) Brief in Opposition to Natus' Motion for Summary Judgment of Invalidity, (2) Opening Brief in Support of Nox Medical's Cross-Motion for Summary Judgment of No Invalidity, and (3) Opening Brief in Support of Nox Medical's Proposed Claim Constructions from Civil Action No. 15-709-RGA, Nox Medical ehf v. Natus Neurology Inc., Jul. 26, 2017, 63 Pages.
Plaintiff Nox Medical EHF's Reply Brief in Further Support of Its Cross-Motion for Summary Judgment of No Invalidity from Civil Action No. 15-709-RGA, Nox Medical ehf v. Natus Neurology Inc., Aug. 23, 2017, 18 Pages.
Order from Civil Action No. 15-709-RGA, Nox Medical ehf v. Natus Neurology Inc., Feb. 13, 2018, 1 Page.
Verdict Form from Civil Action No. 15-709-RGA, Nox Medical ehf v. Natus Neurology Inc., May 7, 2018, 2 Pages.
Natus Neurology Inc.'s Brief in Support of Summary Judgment of Invalidity of the Asserted Claims of U.S. Pat. No. 9,059,532 from Civil Action No. 1:15-709-RGA, Nox Medical ehf v. Natus Neurology Inc., Jul. 7, 2017, 24 Pages.
International Search Report from PCT Application No. PCT/IB2017/053128, dated Aug. 9, 2017.
Minutes of OP and Interlocutory Decision from Application No. 11 758 266.8, Nov. 6, 2017.
Notification of Minutes and Amendments at OP from Application No. 11 758 266.8, Nov. 6, 2017.
OP Decision and Reasoning from Application No. 11 758 266.8, Nov. 6, 2017.
Opposition against EP Application No. 11758266.8, Dec. 16, 2015.
Letter containing Test Results from European Patent No. 2584962, Feb. 23, 2017.
Escobar et al., "Nu-Way Snaps and Snap Leads: an Important Connection in the History of Behavior Analysis," Behav Analyst, 2014, vol. 37, pp. 95-107.
Declaration of Mr. Arni Vilhjalmsson, Apr. 11, 2017, 3 Pages.
Declaration of Mr. Hilmarsson, Apr. 6, 2017, 1 Page.
Declaration of Ms. Ema Sif Amardottir, 1 Page, Apr. 21, 2017.
Agustsson et al., "White Paper RIP Signal Assessment," Apr. 21, 2017, 21 Pages.
Statement of Mr. Sveinbjorn Hoskuldsson, Apr. 24, 2017, 2 Pages.
Statement from Mr. Andres Einar Hilmarsson, Apr. 24, 2017, 1 Page.
Declaration of Ms. Erla S. Amadottir, Apr. 25, 2017. 5 Pages.

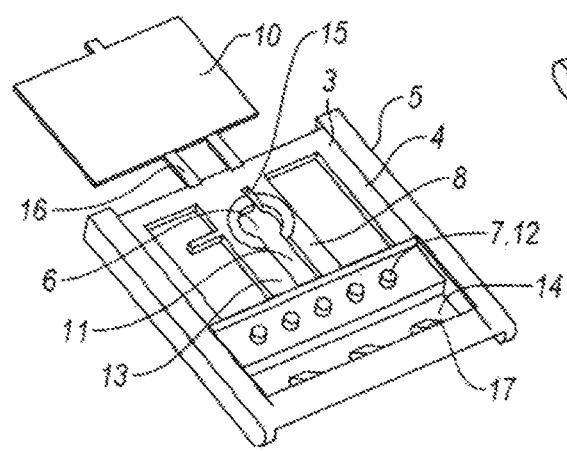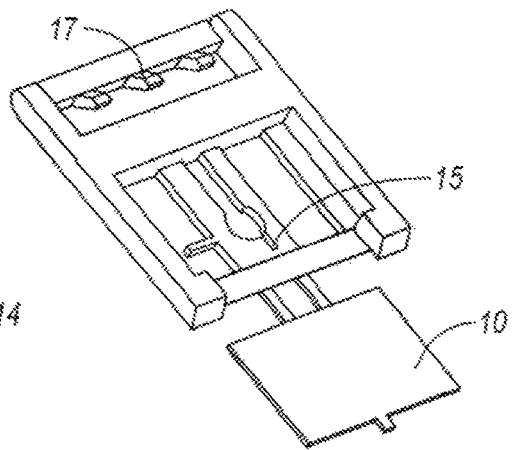
FIG. 1A    FIG. 1B
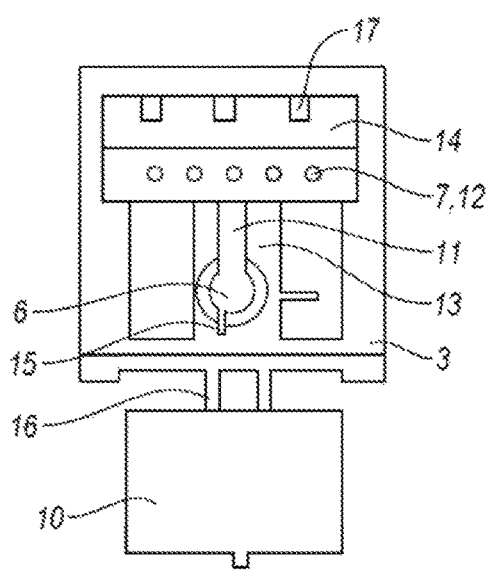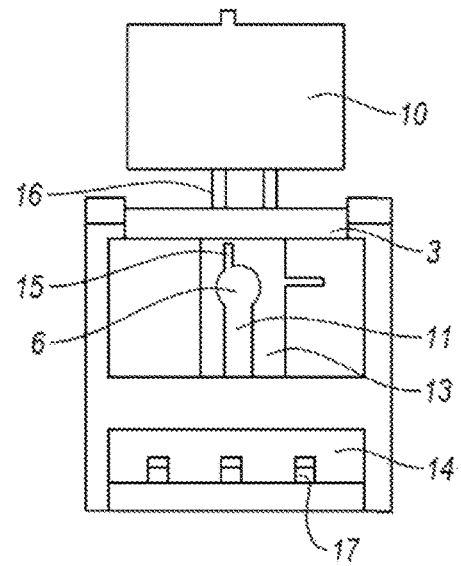
FIG. 1C    FIG. 1D

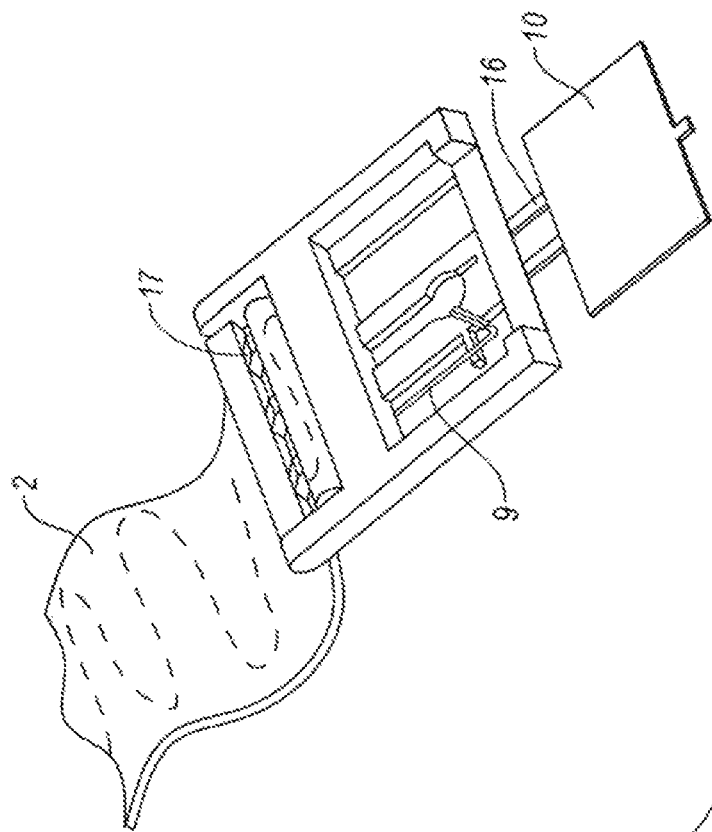
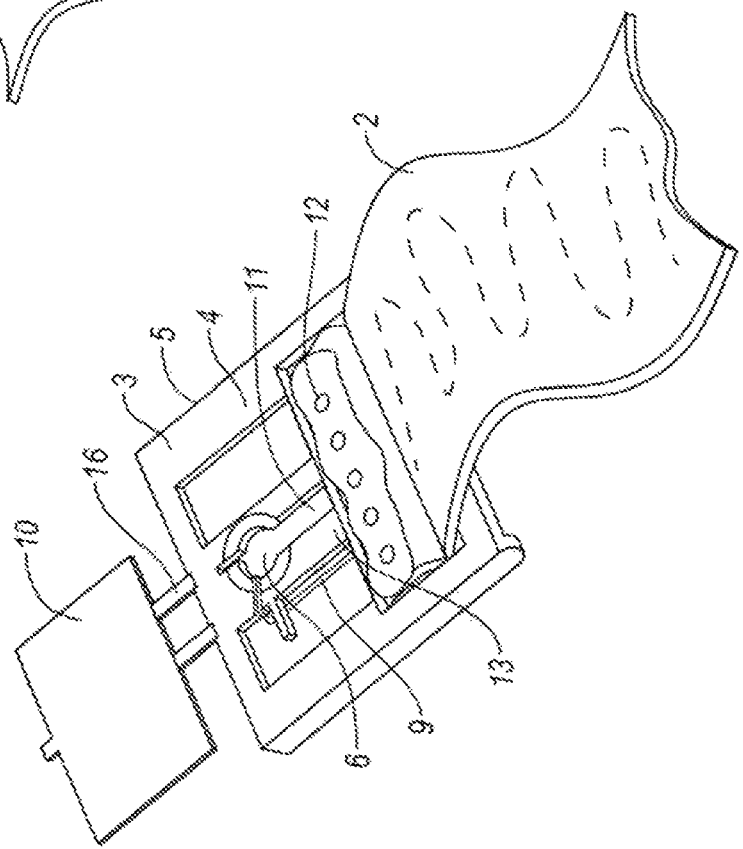
FIG. 2A
FIG. 2B

BIOMETRIC BELT CONNECTOR

This application is a continuation of U.S. patent application Ser. No. 14/733,774, filed Jun. 8, 2015, which is a continuation of U.S. patent application Ser. No. 13/806,834, filed Mar. 18, 2013 (now U.S. Pat. No. 9,059,532), which is a 371 nationalization of Application No. PCT/IS2011/050010 filed Jun. 24, 2011, which claims the benefit of priority of U.S. Provisional Application No. 61/358,472, filed Jun. 25, 2010, the entirety of which are each incorporated herein by reference.

FIELD OF THE DISCLOSURE

The present disclosure is within the field of medical devices, in particular biometric devices for measuring biosignals, and relates particularly to electrodes for such devices and in particular electrode belts and connectors for such belts.

BACKGROUND

Electrode belts are known, both for direct contact galvanic electrodes for measure cardiography signals and inductive belts used in respiratory inductive plethysmography. Prior art belts have various types of connectors, for transmitting the received signal to the respective device. There remains a need for improved belt connectors that are reliable and easy to use and maintain.

SUMMARY

The disclosure provides a belt connector for electrically connecting an electrode belt to a biometric device to be carried on a human or animal body. The belt connector is preferably made from one single piece which can be economically manufactured in order to function as a single-use consumable, to be used with a matching biometric device. The belt connector comprises a molded plastic frame having a front side and a rear side, the frame having a receiving hole, having radial flexibility to function as a female snap button fastener for receiving and fastening on the front side of the frame a male snap protrusion. The belt connector further comprises fastening means for fastening to the frame a belt end of the electrode belt, and a member adjacent to the snap fastener receiving hole to engage an electrode wire end electrically connected to the belt such that the wire end is in electrical contact with the hole, either by extending into the hole or coming in electrical contact e.g. through a bridging conductor, with a conducting male snap fastener inserted in the receiving hole.

The belt connector and belt should be configured such that a person wearing the belt under operation is insulated from current running through the belt, in order to meet existing standards for medical devices. The belt connector of the present disclosure is configured accordingly, and in a preferred embodiment, the belt connector comprises a shield member which is arranged on the rear side of the frame to electrically shield the wire end from the rear side exterior of the belt connector.

The belt connector preferably comprises a cover enclosing the connector and wire end. The cover may suitably include a pre-perforated hole overlapping the hole of the frame, or in other embodiments is made from such material that can readily be perforated by pressing the connector onto a male fastener which fits the receiving hole of the frame.

The belt end is fixedly engaged with the connector and the electrode wire connected to the connector such that the electrode wire is in electrical contact with the female snap fastener hole and thereby comes in electrical contact with a conducting male snap fastener inserted in the hole.

Preferably the belt end is engaged with the connector in a fashion allowing adjustment of the length of the belt.

BRIEF DESCRIPTION OF THE FIGURES

FIGS. 1A, 1B, 1C, and 1D illustrate a belt connector according to a first embodiment.

FIG. 1A shows a prospective top view according to the first embodiment.

FIG. 1B shows a prospective bottom view according to the first embodiment.

FIG. 1C shows a top plan view according to the first embodiment.

FIG. 1D shows a bottom plan view according to the first embodiment.

FIGS. 2A, 2B, and 2C illustrate a belt connector and connected belt according to a second embodiment.

FIG. 2A shows a prospective top view according to the second embodiment.

FIG. 2B shows a prospective bottom view according to the second embodiment.

FIG. 2C shows a prospective top view according to the second embodiment.

DETAILED DESCRIPTION

Figure 2C:
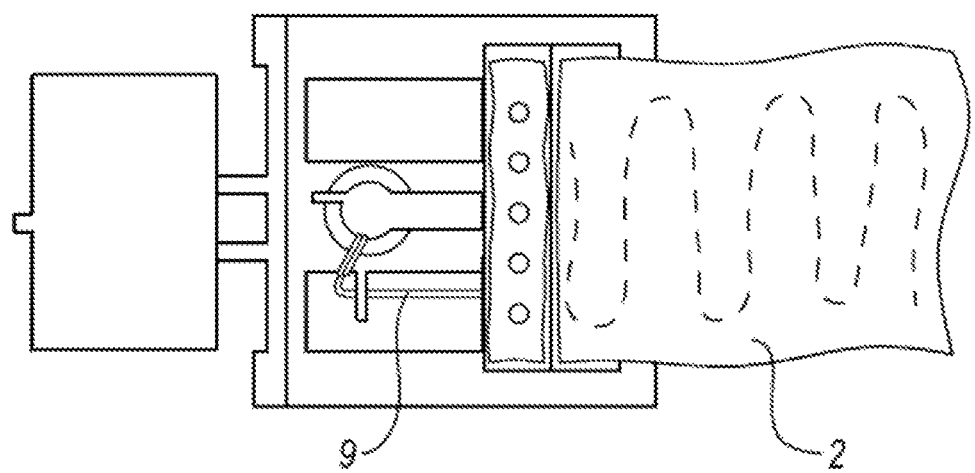

The disclosed belt connector is suitable for various types of electrode belts, such as for cardiographic measurements, both in clinical settings or for training purposes, but also for belts such as RIP (respiratory inductive plethysmography) belts.

As mentioned above, the belt connector is intended for electrically connecting an electrode belt to a biometric device, the term biometric device in this context includes any devices for receiving electrical biosignals as well as extension cables, intermediate devices, connecting boxes, etc. or other means for receiving and transmitting the biosignals.

The belt connector is preferably made from any of various suitable non-conducting plastic materials, such as but not limited to ABS (acrylonitrile butadiene styrene), PC/ABS, polyethylene, e.g. low density polyethylene (LDPE) or high density polyethylene (HDPE), or derivatives such as polyethylene terephthalate (PET) or polyfluoroethylene (PTFE), or more preferably polypropylene, polyvinyl chloride, or polyamide (nylon). In other embodiments the connector is made from paper based material or other material from natural fibers.

The electrode belt is generally a flexible belt such as commonly used in respiratory inductance plethysmography (RIP) devices today. Such electrode belt is preferably a flexible textile belt where an electrode wire is interwoven in the belt or can be laminated between two layers, typically in a zig-zag fashion to allow longitudinal elasticity.

The molded frame of the connector has a front side and a rear side, which are defined as follows: the front side of the frame faces the biometric device which is fastened onto the connector for operation and the rear side faces away from the device. In the presently preferred embodiment the rear side of the connector faces the body of the patient when mounted, i.e. the belt connector comes between the patient and the biometric device. However, the biometric device can also be configured such that the device faces the patient and the belt connectors lie on top of the device, i.e. connect to the device on the face of the device facing away from the patient, thus in such embodiment the front side of the connectors face the patient and the rear side face away from the patient.

The frame has a receiving hole with radial flexibility to function as a female snap button fastener for receiving and fastening on the front side of the frame a male snap protrusion. A mating biometric device will thus have a corresponding mating male snap fastener which can be fastened securely onto the belt connector. The hole can preferably be shaped circular or semi-circular but may in other embodiments have any other suitable shape, such as a general elongated shape shaped by two parallel members, suitably including guiding members to ensure proper positioning of the mating male snap member, a square opening, or the like.

The radial flexibility of the hole can in one embodiment be achieved by one or more slot extending from the hole. The embodiment shown if FIGS. 1 and 2 shows two slots extending across from each other in the belt direction. The one or more slot are preferably formed by at least one elongated member having flexibility transverse to its longitudinal axis (e.g. by being sufficiently thin), thus imparting flexibility to the width of the hole. Preferably the hole is between two elongated members where one or both have sufficient and suitable flexibility to provide a snap fastener hole with suitable fastening strength.

As mentioned, the belt connector comprises a member adjacent to the snap fastener receiving hole to engage an electrode wire coming from the belt end. This wire must come in electrical contact with the receiving hole, either by extending into the hole or coming in electrical contact with the hole e.g. through a bridging conductor. In one embodiment, the wire end is crimped onto the member such the crimping tubing fixes the wire and conducts and connects electrically the wire to the receiving hole, such that thus the wire and the belt is in electrical contact with a conducting male snap fastener inserted in the receiving hole.

The slot mentioned above can also function to provide an additional opening for a mating male projection on the biometric device. By this arrangement it is assured that the device cannot be incorrectly fastened, and the device will not fit any generic non-proprietary belts having connectors with female fasteners but without the correctly shaped and placed extended hole.

The connector frame has in another embodiment a separate further hole, not joined to the main fastener and electrical connection hole, where the further hole can mate with a corresponding male projection on the biometric device. Alternatively, the biometric device can have a female hole for mating with a corresponding male projection on the belt connector.

The connector frame further comprises fastening means for fastening to the frame a belt end of an electrode belt. The fastening means can in one embodiment comprise a slot with a row of teeth, pins or hooks, transverse to the belt direction, to engage a belt end. The slot preferably allows to insert through it a loop of the belt such that the belt length is adjusted and fixed, but preferably so that a user can later re-adjust the length.

In another embodiment, the fastening means comprise a ridge member, which can be a flat or sharp elongated ridge or ridge or row comprising pins or hooks, which ridge lies transverse to the belt direction and to which a belt end can be fastened onto with heat melting or gluing. Alternatively, the ridge member can have pins hooks that grab onto the belt fabric without need of heating.

Preferably, the frame has also an adjustment slot for user adjustment of the belt, which can configured with either of the two described fastening means, the adjustment slot having a row of teeth, pins or hooks transverse to the belt direction, through which adjustment slot a loop of the belt can be inserted, which hooks onto the teeth/pins when pulled on, such that the length of the belt can be readily adjusted but also secured in the desired adjusted length.

Figure 3A:
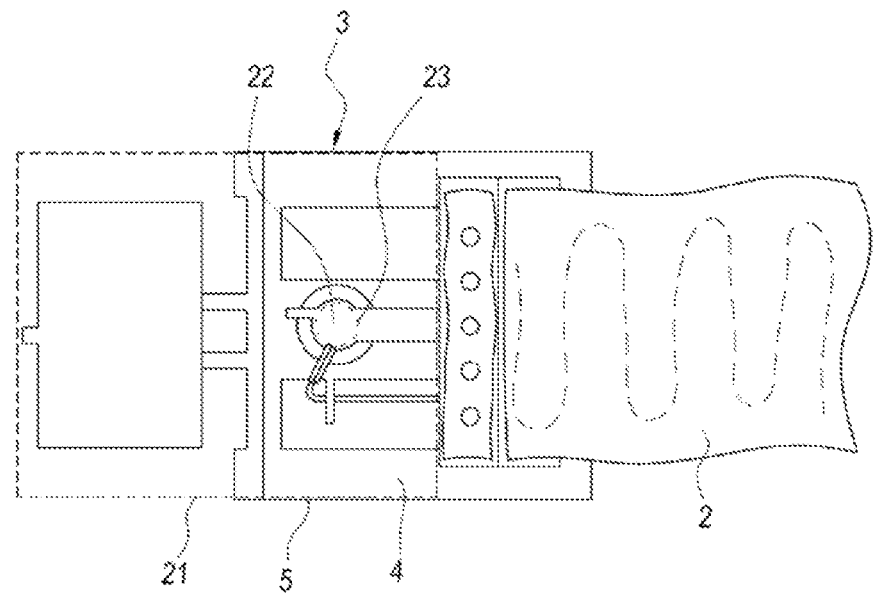
FIG. 3A shows a top plan view according to another embodiment.
Figure 3B:
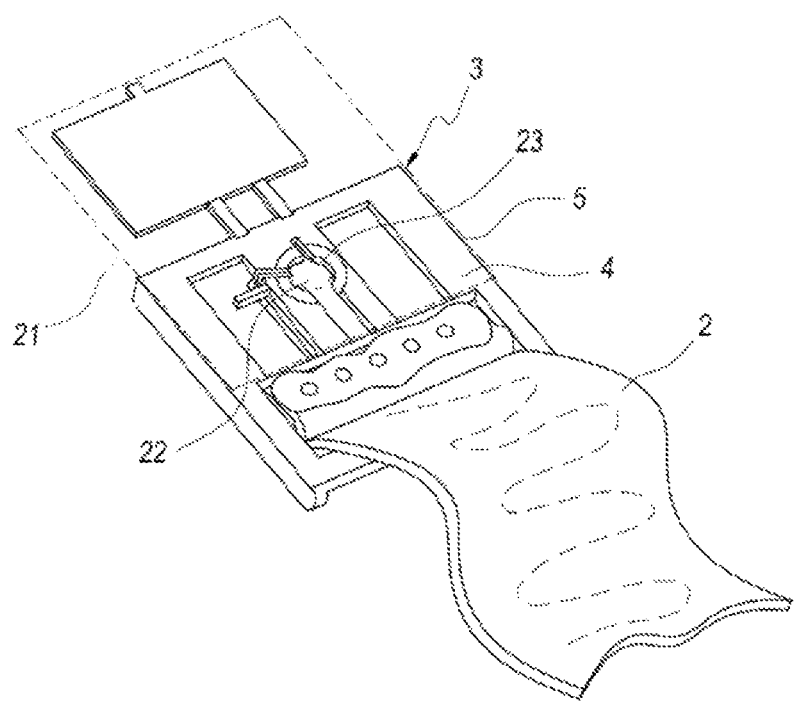
FIG. 3B shows a prospective top view according to the embodiment of FIG. 3A.

As shown in the embodiment of FIGS. 3A and 3B, the connector will preferably include a cover 21 substantially or essentially fully enclosing the frame 3, which cover 21 either includes a pre-made hole 22 overlapping the receiving hole 6 of the frame, or can be readily perforated 23 by pressing the connector onto a male fastener which fits the receiving hole 6 of the frame 3. A suitable cover can be arranged by a suitably sized paper, plastic or fabric sticker (foldable sheet with glue on one side) which sticker is folded over the frame after the belt end has been fastened and the wire end electrically connected to the receiving hole, or the cover can be from but not limited to a paper envelope, a plastic envelope and a textile envelope, which envelope is suitably fastened by gluing, sewing or the like.

In the embodiments where the biometric device has a further male projecting member which fits within the slot of the frame or within a separate mating hole, the cover is suitably arranged with corresponding openings for such hole or slot for receiving such mating male member, and the cover may also have a suitable hole allowing the protrusion of a male protruding member being a part of the frame which fits in a mating receiving hole or slot on the mating biometric device.

In a preferred embodiment, the connector comprises a shield member which is arranged on the rear side of the frame to electrically shield the wire from the rear side exterior of the belt connector. The shield member is in one embodiment a sheet member extending from the frame, which sheet member is configured to be folded over onto the rear side of the frame to cover the hole and engaged wire. Such shield member molded in one piece with the frame with enough 30 strength but suitably flexible to allow folding at least once without braking allows the use of a cover enclosing the frame, which cover need not be electrically insulating, as the shield insulates the only part of the connector which could conduct electrical current of the connector, except through the hole.

In another aspect, the present disclosure sets forth a process for making an electrode belt with biometric belt connectors, comprising:

placing an end of a flexible electrode belt with an incorporated wire onto a belt connector as defined above, in the suitable direction in which it is to be fastened onto the connector, such that a portion of the belt end extends beyond the ridge member or row of pins, pressing a heat element ultrasonic hot body or other means of heat transfer onto the belt and ridge member, and through the action of the heat, shearing an end piece of the belt but leaving intact the incorporated wire, thus revealing an end of the wire, through the action of heat from the heat element, fastening by heat melting the belt to the ridge, and fastening the wire end to a member adjacent to the hole of the connector frame, such that the end is in electrical contact with the hole and comes in electrical contact with a conducting male snap fastener inserted in the hole.

The process further preferably comprises enclosing the connector frame with the fastened belt end and connected wire with a cover such as suitably a cover as described above.

FIGS. 1A, 1B, 1C, and 1D illustrate a belt connector according to a first embodiment. FIG. 1A shows a prospective top view according to the first embodiment.

FIG. 1B shows a prospective bottom view according to the first embodiment. FIG. 1C shows a top plan view according to the first embodiment. FIG. 1D shows a bottom plan view according to the first embodiment.

FIGS. 2A, 2B, and 2C illustrate a belt connector and connected belt according to a second embodiment.

FIG. 2A shows a prospective top view according to the second embodiment.

FIG. 2B shows a prospective bottom view according to the second embodiment.

FIG. 2C shows a prospective top view according to the second embodiment.

As seen in the first and second embodiments of FIGS. 1A, 1B, 1C, and 1D and FIGS. 2A, 2B, and 2C, respectively, a biometric belt connector (1) is electrically connected to an electrode belt (2). The connector (1) may comprise a molded plastic frame (3) having a front side (4) and a rear side (5), a shaped circular or semi-circular hole (6) with radial flexibility to function as a female snap button fastener, fastening means (7) which comprise a ridge member (12). According to the first embodiment, the ridge member (12) may include a series of buts which are provided transverse to the belt direction and to which the belt end can be fastened onto with heat melting or gluing. The frame (3) may include two members (8, 13) adjacent to the hole (6), the two members (8, 13) forming a slot (11) extending from the hole and a second slot (15) across from the first slot (11).

The elongated members and slots provide the hole with sufficient flexibility (i.e. elasticity in the width of the hole) to function as a female snap fastener. The member (13) also functions to engage an electrode wire end (9) from the belt end electrically connecting the belt with the hole and which comes in electrical contact with a conducting male snap fastener inserted in the hole. The connector further comprises a belt slot (14) with teeth members or pins (17), through which slot a loop of the belt (2) can be inserted such that it is held by the teeth/pins when pulled back, to adjust the length of the belt.

The connector further comprises a shield member (10) which may be molded in one piece with the frame (3) and joined to the frame with foldable hinges (16) such that the shield member can be folded over to cover the rear side of the hole and wire end.

What is claimed:

1. An electrode belt connector for electrically connecting a conductor of an electrode belt to a snap electrode, the belt connector comprising:
   a plastic frame including a first elongated member and a second elongated member, the first elongated member and the second elongated member defining a receiving hole configured to receive and fasten the plastic frame to a protrusion of the snap connector electrode; and
   a fastener portion configured to couple the electrode belt connector to the electrode belt,
   wherein
   the first elongated member and the second elongated member further define a first slot extending from the receiving hole,
   the first elongated member and/or the second elongated member provide a radial flexibility to the receiving hole, and
   the first elongated member engages the conductor of the electrode belt by the conductor extending into the receiving hole such that the conductor is in electrical contact with the protrusion of the snap connector electrode upon penetration of the protrusion into the receiving hole.

2. The electrode belt connector according to claim 1, wherein the first elongated member and the second elongated member are arranged generally in a first plane, and
   the first elongated member is configured to engage the conductor of the electrode belt by at least an end portion of the conductor extending through the receiving hole from a first side of the first plane to a second side of the first plane, the first side of the first plane being opposite from the second side of the first plane, such that when the protrusion of the snap connector electrode penetrates the receiving hole, the end portion of the conductor is forced into physical contact with at least a lateral surface of the protrusion of the snap connector electrode.

3. The electrode belt connector according to claim 1, wherein the radial flexibility provides the force that forces the conductor into physical contact with at least a lateral surface of the protrusion of the snap connector electrode when the protrusion of the snap connector electrode penetrates the receiving hole.

4. The electrode belt connector according to claim 1, wherein an end portion of the conductor of the electrode belt is at least partially wrapped around the first elongated member at least once.

5. The electrode belt connector according to claim 1, wherein the end portion of the conductor of the electrode belt is wrapped around the first elongated member such that an end portion of the conductor passes from the first side of the first plane to the second side of the first plane two or more times.

6. The electrode belt connector according to claim 1, wherein the plastic frame is a molded plastic frame.

7. The electrode belt connector according to claim 1, further comprising a shield member arranged on a rear side of the plastic frame, the shield member being arranged generally in a second plane, the second plane being parallel to the first plane, wherein the shield member is configured to electrically shield the conductor of the electrode belt and an end portion of the conductor from the rear side exterior of the belt connector.

8. The electrode belt and the belt connector of claim 7, wherein
   said shield member includes a sheet member extending from the plastic frame, and
   the sheet member is configured to be folded over onto the rear side of the frame to cover the rear side of the receiving hole and engaged conductor.

9. The electrode belt connector according to claim 1, wherein a second slot extends from the receiving hole, the second slot extending generally from an opposite side of the receiving hole than the first slot, and the radial flexibility is provided in part by the second slot.

10. The electrode belt connector according to claim 9, wherein the radial flexibility is provided in part by the second slot.

11. The electrode belt connector according to claim 1, wherein the radial flexibility provided by the first elongated member and/or the second elongated member imparts a tension force transverse to a longitudinal axis of the first elongated member and/or the second elongated member upon penetration of the protrusion of the snap connector electrode into the receiving hole.

12. The electrode belt connector according to claim 1, further comprising a cover enclosing the frame, wherein
the cover includes a hole overlapping the receiving hole of the frame, or
the cover is configured to be readily perforated by pressing the belt connector onto the protrusion of the snap connector electrode.

13. The electrode belt connector according to claim 12, wherein the cover includes a folded paper, a plastic sticker, a fabric sticker, a plastic envelope, or a textile envelope.

14. The electrode belt connector according to claim 1, wherein the fastener portion includes a slot with a row of teeth, pins, or hooks that extend transverse to the belt direction, the row of teeth, pins, or hooks being configured to engage an end portion of the electrode belt.

15. The electrode belt connector according to claim 1, wherein the belt connector comprises an adjustment slot with teeth, pins, or hooks, and
wherein a loop of desired length of the belt can be inserted through the adjustment slot, to adjust and fix the length of the electrode belt.

16. The electrode belt connector according to claim 1, wherein the end portion of the conductor of the electrode belt is an electrode wire of the electrode belt.

17. An electrode belt configured to be electrically connected to a snap connector electrode connected to a biometric device, the belt comprising:
a flexible belt having a conductor; and
a belt connector configured to electrically connect the conductor of the flexible belt to a protrusion of the snap connector electrode,
wherein the electrode belt connector includes
a plastic frame including a first elongated member and a second elongated member, the first elongated member and the second elongated member defining a receiving hole configured to receive and fasten the plastic frame to a protrusion of the snap connector electrode, and
a fastener portion configured to couple the electrode belt connector to the electrode belt, wherein
the first elongated member and the second elongated member further define a first slot extending from the receiving hole,
the first elongated member and/or the second elongated member provides a radial flexibility to the receiving hole, and
the first elongated member engages the conductor of the electrode belt such that the conductor is in electrical contact with the protrusion of the snap connector electrode by the conductor extending into the receiving hole.

18. The electrode belt according to claim 17, wherein the belt connector belt is a flexible textile belt with an electrode wire interwoven in the belt or laminated between two layers of the belt.

19. The electrode belt and the belt connector of claim 18, wherein the end portion of the conductor of the electrode belt is an end portion of the electrode wire.

20. A method for making an electrode belt with an electrode belt connector that is configured to electrically connect a conductor of the electrode belt to a snap connector electrode connected to a biometric device, the method comprising:
providing a belt connector that includes a plastic frame and a fastener portion,
the plastic frame including a first elongated member and a second elongated member, the first elongated member and the second elongated member defining a receiving hole configured to receive and fasten the plastic frame to a protrusion of the snap connector electrode,
the first elongated member and the second elongated member further defining a first slot extending from the receiving hole,
the first elongated member and/or the second elongated member providing a radial flexibility to the receiving hole, and
the first elongated member being configured to engage the conductor of the electrode belt such that the conductor is in electrical contact with the protrusion of the snap connector electrode by the conductor extending into the receiving hole;
placing an end portion of a flexible electrode belt with a wire incorporated therein onto the fastener portion of the belt connector such that an end portion of the belt end extends beyond a ridge member or row of pins of the fastener portion;
pressing a heat element, an ultrasonic hot body, or a heat transfer unit onto the belt and ridge member or row of pins such that through the action of heat, an end piece of the belt is sheared while leaving intact the incorporated wire within the end piece, thus revealing an end of the wire;
fastening by heat melting the belt to the ridge through the action of the heat; and
fastening the wire end to the first elongated member such that the wire end is in electrical contact with the hole.

* * * * *